United States Patent [19]

Wood

[11] Patent Number: 5,298,606
[45] Date of Patent: Mar. 29, 1994

[54] PROCESS FOR THE PREPARATION OF SUBSTITUTED AZOXYCYANIDES

[75] Inventor: William W. Wood, Sittingbourne, England

[73] Assignee: Shell Research Limited, United Kingdom

[21] Appl. No.: 889,240

[22] Filed: May 28, 1992

[30] Foreign Application Priority Data

Jun. 13, 1991 [GB] United Kingdom ............... 9112696

[51] Int. Cl.$^5$ .............. C07C 245/02; C07C 245/20; C07C 291/08; C07C 255/67; A01N 33/26
[52] U.S. Cl. ................................. 534/556; 534/616
[58] Field of Search ........................ 534/566, 616

[56] References Cited

U.S. PATENT DOCUMENTS 3,419,540 12/1968 Feltzer et al. ................ 534/566
5,084,448 1/1992 Gray et al. .................. 534/566 X

FOREIGN PATENT DOCUMENTS 411719 2/1991 European Pat. Off. ......... 534/566
51-11735 1/1976 Japan ........................ 534/566
51-26844 3/1976 Japan ........................ 534/566

OTHER PUBLICATIONS

Hayashi et al., J. Pharm. Soc. Japan, vol. 85, pp. 475 to 476 (1965).

Primary Examiner—Floyd D. Higel

[57] ABSTRACT

A process for the preparation of a compound of general formula

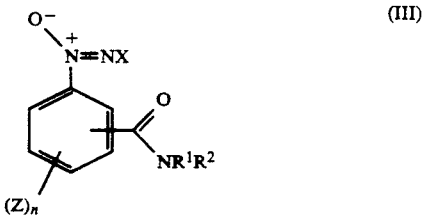

wherein X represents a cyano group, a group —COOH or a salt, ester or amido derivative thereof, $R^1$ represents a hydrogen atom or an optionally substituted alkyl group, $R^2$ represents an optionally substituted alkyl or phenyl group, Z represents an alkyl group or a halogen atom and n represents 0, 1, 2, 3 or 4, the process comprising reacting a compound of general formula

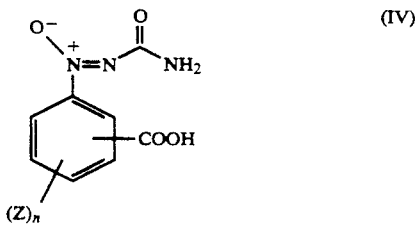

with a first reactant capable of both dehydrating the amide group of said compound of general formula IV, to form a group X wherein X represents a cyano group, and reacting with the carboxy group of said compound of general formula IV to form a group with which a compound of general formula $R^1R^2NH$ may react; subsequently reacting the resulting compound with a compound of general formula $R^1R^2NH$ to form a compound of general formula III wherein X represents a cyano group; and optionally derivatizing that compound to form other compounds of general formula III, is disclosed.

10 Claims, No Drawings

PROCESS FOR THE PREPARATION OF SUBSTITUTED AZOXYCYANIDES

This invention relates to a process for the preparation of biocidal compounds, and particularly, although not exclusively, to a process for the preparation of amido-substituted phenyl azoxycyanides.

European Patent Specification No. 0 411 719 A (Shell) discloses compounds of general formula R—N=NX or N-oxides thereof, wherein R represents an amidophenyl group and X represents, for example, a cyano group. Such compounds are stated to be made by reacting a compound of general formula R—N=O with cyanamide.

The present invention relates to a novel process for the production of amido-substituted phenyl azoxycyanides. The process is based upon the discovery that a compound of formula

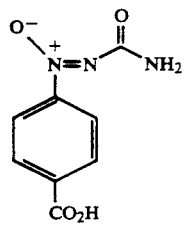

may be reacted with thionyl chloride and subsequently quenched with aniline to produce a compound of general formula

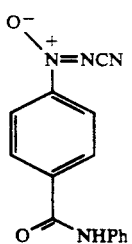

It is believed that, in the reaction, thionyl chloride both dehydrates the amide group to form a nitrile group and reacts with the carboxylic acid group to form an acid chloride group. Then, it is believed, aniline reacts with the acid chloride group to form an amide group.

Thus, in accordance with the invention, there is provided a process for the preparation of a compound of general formula

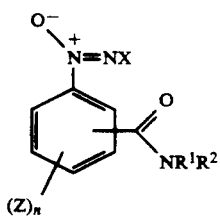

wherein X represents a cyano group, a group —COOH or a salt, ester or amido derivative thereof, $R^1$ represents a hydrogen atom or an optionally substituted alkyl group, $R^2$ represents an optionally substituted alkyl or phenyl group, Z represents an alkyl group or a halogen atom and n represents 0, 1, 2, 3 or 4, the process comprising reacting a compound of general formula

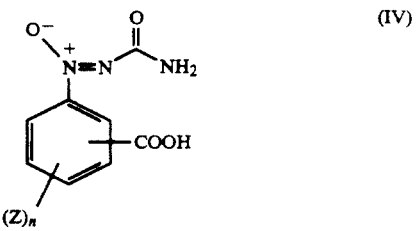

with a first reactant capable of both dehydrating the amide group of said compound of general formula IV, to form a group X wherein X represents a cyano group, and reacting with the carboxy group of said compound of general formula IV to form a group with which a compound of general formula $R^1R^2NH$ may react; reacting the resulting compound with a compound of general formula $R^1R^2NH$ to form a compound of general formula III wherein X represents a cyano group; and optionally derivatising that compound to form another compound of general formula III.

Suitably, said first reactant is capable of both dehydrating the amide group of said compound of general formula IV and halogenating, preferably chlorinating, the carboxy group to form an acid halide, suitably an acid chloride, group with which said compound of general formula $R^1R^2NH$ may react.

Suitably, said first reactant is selected from thionyl chloride, phosphorus trichloride, phosphorus pentachloride and phosphorus oxychloride. Most preferably, said first reactant is thionyl chloride.

Suitably, said first reactant and said compound of general formula $R^1R^2NH$ are in molar excess relative to the quantity of said compound of general formula IV. Suitably, up to 5, preferably up to 3, molar equivalents of said first reactant are provided per molar equivalent of said compound of general formula IV. Suitably, up to 5, preferably up to 3.5, molar equivalents of said compound of general formula $R^1R^2NH$ are provided per molar equivalent of said compound of general formula IV.

The process is suitably carried out at a temperature in the range 0° C. to 100° C., preferably in the range 20° C. to 60° C. More preferably, the process, particularly the reaction of a compound of general formula IV with said first reactant, is carried out at elevated temperature i.e. above ambient temperature, for example at about 40° C.

Suitably, said compound of general formula IV is dissolved in an aprotic solvent, preferably an ethereal solvent, for example, tetrahydrofuran. Desirably, dry solvent is used. Said first reactant, preferably thionyl chloride, is then added, preferably slowly, for example, dropwise. The reactants are suitably stirred for a period of time, for example, about 3 hours, whilst maintaining the temperature within the aforementioned range.

The reaction mixture is then suitably quenched, conveniently at ambient temperature, with said compound of general formula $R^1R^2NH$ and the mixture stirred for a time, for example, about 20 minutes.

The compound of general formula III may be isolated by precipitation, by pouring the reaction mixture into water. The precipitate may be collected and purified by standard techniques.

Derivatisation of a compound of general formula III in which X represents a cyano group, may, for example, be effected by standard techniques. Thus, for example, by standard hydrolysis, in the presence of a strong acid or a strong base, the cyano group may be converted to a carboxy group, or, stopping the reaction at an intermediate stage, an amido group. Esters may be prepared by standard esterification of the resultant carboxylic acid or by acid alcoholysis of the cyano compound to form the acid salt of the imidate ester, which is reacted with water, suitably at ambient temperature, to yield the ester.

Compounds of general formula IV are known or may be prepared from known compounds by standard methods, for example, as described in JP 7771444 (Chem. Abs.87:167770j) and JP 74082058 (Derwent No 76-19656X). Compounds of general formula $R^1R^2NH$ also are known or preparable from known compounds by standard techniques.

Unless otherwise specified in this specification, an alkyl moiety may be linear or branched and suitably contains up to 12, preferably up to 6, and most preferably up to 4 carbon atoms.

Unless otherwise stated in this specification, when any groups are designated as being optionally substituted, the substituent groups which are optionally present may be any of those customarily employed in the development of biocidal compounds, and/or the modification of such compounds to influence their structure/activity, persistence, penetration or other property. In relation to an alkyl group specific examples of such substituents may include halogen, especially fluorine, chlorine or bromine atoms, and phenyl, alkoxy, hydroxy, cyano and (alkyl)amino groups. In relation to a phenyl group optional substituents may include halogen atoms, for example fluorine, chlorine, bromine and iodine atoms, and nitro, cyano, alkoxy, hydroxy, (alkyl)amino, alkyl and haloalkyl (especially $CF_3$) groups. Typically, 0–3 substituents may be present, most commonly 0 or 1.

Suitably, X represents a cyano group; a group —COOH or a metal salt thereof; a group —COOR$^3$, in which R$^3$ represents a $C_{1-4}$ alkyl or $C_{2-4}$ alkenyl or alkynyl group, for example methyl, ethyl, allyl or propargyl; or an amido group —CONH$_2$. Preferably, X represents a cyano group.

Suitably, R$^1$ may represent a hydrogen atom or an optionally substituted, preferably unsubstituted, alkyl group. Suitably, R$^2$ may represent an optionally substituted, preferably unsubstituted, alkyl group or phenyl group. Where said phenyl group is substituted, suitably it is substituted by one or more halogen atom(s), alkoxy, haloalkyl and/or alkyl group(s). Preferably, R$^1$ represents a hydrogen atom or methyl group and R$^2$ represents an alkyl, phenyl, chlorophenyl, methoxyphenyl or (trifluoromethyl)phenyl group.

Wherein R$^2$ represents an optionally substituted phenyl group, suitably only one substituent is present which substituent is preferably located in the para-position.

Z may represent a methyl group or a chlorine atom. Suitably, n may represent 1 or, most preferably, 0.

Preferably, the substituted amido group —CONR$^1$R$^2$ is located para to the azoxy group.

The invention extends to a compound of general formula III when prepared by a process as described herein.

Compounds of general formula III are fungicidal, and are described in EP-A-411 719.

The invention will now be further illustrated by the following example.

EXAMPLE

Preparation of [4-(N-phenylamido)phenyl]-ONN-azoxycyanide ($R^1$=H; $R^2$=phenyl; X=cyano; n=0)

4-Carboxyphenyl-ONN-azoxyformamide (1.85 g, 0.009 mol) was dissolved in dry tetrahydrofuran (40 ml) at 40° C. and thionyl chloride (2.8 g, 1.8 ml, 0.024 mol) was added dropwise. The reaction mixture was stirred for three hours at 40° C. The mixture was allowed to cool to ambient temperature and quenched with aniline (3 ml, 2.9 g, 0.03 mol) followed by stirring for a further 20 minutes. The reaction mixture was then poured into water and a yellow precipitate collected.

The compound obtained as the precipitate was characterized as [4-(N-phenylamido)phenyl]-ONN-azoxycyanide by comparison of its $^1$H n.m.r. spectrum with that of an authentic sample. Yield 38%. M+(CI):267 (M+ +H).

I claim:

1. A process for the preparation of a compound of formula

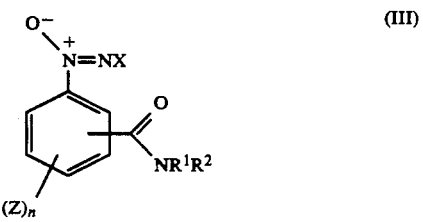

(III)

wherein X represents cyano, —COOH or a metal salt thereof, —COOR$^3$ or CONH$_2$; R$^1$ represents hydrogen or alkyl, each unsubstituted or substituted by substituents selected from the group consisting of halogen, phenyl, alkoxy, hydroxy, cyano and alkylamino; R$^2$ represents alkyl either unsubstituted or substituted by substituents selected from the group consisting of halogen, phenyl, alkoxy, hydroxy, cyano and alkylamino or phenyl each unsubstituted or substituted by substituents selected from the group consisting of halogen, nitro, cyano, alkoxy, hydroxy, alkylamino, alkyl and haloalkyl; R$^3$ represents $C_{1-4}$ alkyl, $C_{2-4}$ alkenyl or $C_{2-4}$ alkynyl; Z represents an alkyl group or a halogen atom and n represents 0, 1, 2, 3 or 4, the process comprising reacting a compound of formula

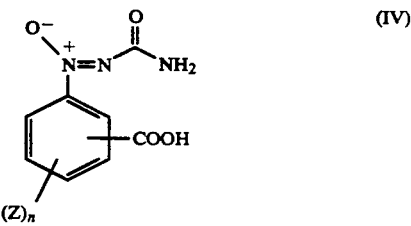

(IV)

with a first reactant capable of both dehydrating the amide group of said compound of formula IV, to form a group X wherein X represents cyano, and halogenating the carboxy group of said compound of formula IV to form an acid halide group; reacting the resulting compound with a compound of formula $R^1R^2NH$ to form a compound of formula III wherein X represents cyano; or further hydrolyzing a compound of formula III wherein X is cyano to form a compound of formula III wherein X is —COOH or —CONH$_2$; or further, esterifying a compound of formula III wherein X is —COOH to form a compound of formula III wherein X is —COOR$^3$; or further reacting a compound of formula III wherein X is —COOH with a metal or metal salt to form a compound of formula III wherein X is a metal salt of —COOH.

2. A process as claimed in claim 1, wherein said first reactant is capable of both dehydrating the amide group of said compound of formula IV and chlorinating the carboxy group to form an acid chloride group.

3. A process as claimed in claim 2, wherein said first reactant is selected from thionyl chloride, phosphorus trichloride, phosphorus pentachloride and phosphorus oxychloride.

4. A process as claimed in claim 3, wherein said first reactant is thionyl chloride.

5. A process as claimed in claim 1, wherein said first reactant and said compound of general formula R$^1$R$^2$NH are in molar excess relative to the quantity of said compound of formula IV.

6. A process as claimed in claim 1, wherein the process is carried out at a temperature in the range 0° C. to 100° C.

7. A process as claimed in claim 1, wherein X represents a cyano group.

8. A process as claimed in claim 1, wherein R$^1$ represents a hydrogen atom or methyl group and R$^2$ represents an alkyl, phenyl, chlorophenyl, methoxyphenyl or (trifluoromethyl)phenyl group.

9. A process as claimed in claim 1, wherein Z represents a methyl group or a chlorine atom.

10. A process as claimed in claim 1, wherein n represents 0.

* * * * *